United States Patent [19]

Peck

[11] Patent Number: 5,604,111

[45] Date of Patent: Feb. 18, 1997

[54] METHOD AND KIT FOR DETECTION OF OXALATE

[75] Inventor: Ammon B. Peck, Gainesville, Fla.

[73] Assignee: University of Florida Research Foundation, Gainesville, Fla.

[21] Appl. No.: 262,424

[22] Filed: Jun. 20, 1994

[51] Int. Cl.$^6$ .............................. C12Q 1/48; G01N 33/53
[52] U.S. Cl. ............................................. 435/15; 435/7.91
[58] Field of Search ........................... 435/7.91, 15, 810, 435/975

[56] References Cited

U.S. PATENT DOCUMENTS 4,539,118   9/1985   Crider ..................................... 210/683

OTHER PUBLICATIONS

Binette, Y., Concentration of Urinary Oxalates: Comparison of Three Methods, Ann Biochim Clin Que 24 (3) 93–96 1985.

Infantes, J., Kinetic–Enzymatic Determination of Oxalate . . . Analytica Chimica Acta 242 (1991) 179–183.

Costello J., Determination of Evolved $^{14}CO_2$. . . Anal Biochem 202 337–339 (1992).

*Primary Examiner*—Ralph Gitomer
*Attorney, Agent, or Firm*—Saliwanchik & Saliwanchik

[57] ABSTRACT

The subject invention concerns the novel use of formyl-CoA transferase enzyme together with oxalyl-CoA decarboxylase enzyme for the detection and measurement of oxalate in biological samples. The use of the enzyme system according to the subject invention results in the conversion of oxalate into carbon dioxide and formate. Because the production of formate is directly correlated to the concentration of oxalate present in a sample, the determination of the resulting formate concentration provides an accurate, sensitive and rapid means for detecting even low levels of oxalate.

6 Claims, 5 Drawing Sheets

FIG. 2

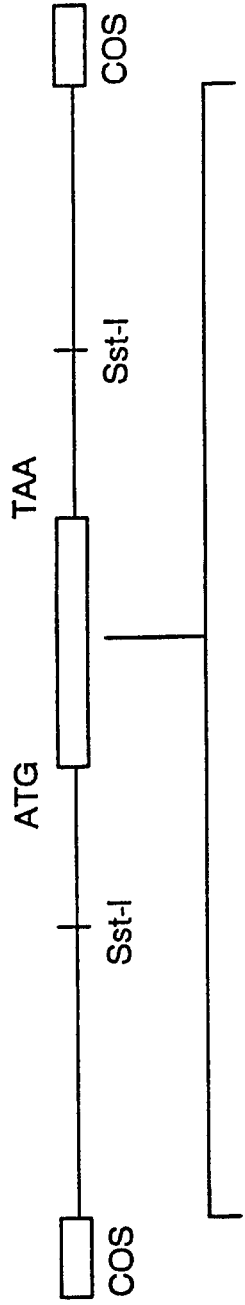

```
        M  T  K  P  L  D  G  I  N  V  L  D  F  T  H  V  Q  A  G  P  A
    ATGAC.AA.CC...GA.GG.AT.AA.GT...GA.TT.AC.CA.GC.GG..CC.GC......CGACTGTGATATATGCGAACTGCAGTGGTCTGATATCGT

AGATGGATATCTTTATGTCGAGCAAGCCCCACAGGCGTAAAAATTGCCATCCAACAGCATTGATGCTCTCCGAATAACAATGAAGGAAACACTTGATAA

ATGCAAAGAGATTCTTGGCGGAGAAACCATAATTGCATCTACTCGTCGCGAACCGCTTTCATCCGGACACAGTATCAAGGTATTTTATGCGCGACGAAAGCATCAGG

TCTTTCCTTCGAAGGGGATACTCTAGAACCTTGTCGACGTCCTGCCTGTACACAGATGATGGGTTTCTTGGGCCAAACGTCATCAAGATTGAAAGACGTGGTTCCGG

AGATATGACTCGTGGATGNCTGCGAGGACAACGAAATGTTGATTCCCTGTATTTCACGATGTTCAACTGTAACAACGTTGATTGAACTGGACATGAAAACCCCGGA

G  K  E  L  L  E  Q  M  I  K  K  A  D  V  M  V  E  N  F  G  P  G  A  L  D  R  M  G  F  T  W  A
    AGGCAAAGAGCTTCTGGAACAGATGATCAAGAAAGCCGACGTCATGGTCGAAAACTTCGGACCAGGCGCACTGGACCGTATGGGCTTTACCTGGCC......CTTAA

CCGAACCAGGCGTCGAAGATGGTATTTCAATGAAAACAACCCCGTCATTATCCGGACTGCCGAAATCTCGATTGTAACGACGAGAACTCCTGCACCGTTGGTGT

CTGGAAGGATATGGGCTGGCCTGGCGTTCGACACGTAAACTGTCACCGTACTGACGATTACGCCCTTCCCAACTACGACAT

CATGGGAGTTTACCCCCAGCAAAGATCCCTCCCCTTGAAACCCGTCTGTCCATGTCCGG.....TAA
```

FIG. 3A

```
-180              -172                    -139                    -124                    -100      -91      -81
     ATTTGTTTAAATTGACCTGAATCAATATTGCCGGATTGATCTAGGTCAATGAATGCAAATTGACTTATGTCAATGGTGCCAAATTGACCTAGGTCAACGG
                             -51                              -32                       -14              M S N D D N V
-80                                                                                                                20
     GATTTTTAAAGGGTATGCGGCATACTCGGAATTGACGTTAAACAACGTTTATCAAACCAACCAAAGAAAGGTATTACTCATGAGTAACGACGACAATGT   120
21   E L T D G F H V L I D A L K M N D I D T M Y G V V G I P I T N L A
     AGAGTTGACTGATGGCTTTCATGTTTTAGATGCCCTGAAAATGAATGACATCGATACCATGTATGGTGTTGTCGGCATTCCTATCACGAACCTGGCT    220
121  R M W Q D D G Q R F Y S F R H E Q H A G Y A A S I A G Y I E G K P
     CGTATGTGGCAAGATGACGGTCAGCGTTTTTACAGCTTCCGTCACGAACACCAACGGTTATGCGCCGGTTACATCGAAGGAAACCTG              320
221  G V C L T V S A P G F L N G V T S L A H A T T N C F P M I L L S G S
     GGCGTTTGCTTGACCGTTTCCGCCCCTGGCTTCCTGAACGGTGTTACTTCCCTGGCTCATGCAACCACCAACTGCTTCCCAATGATCCTGTTGAGCGGTTC  420
321  S E R E I V D L Q Q G D Y E E M D Q M N V A R P H C K A S F R I N
     CAGTGAACGTGAAATCGTCGATTTCCAAGACGGCGATTACGAAGAAATGGATCAGATGTTGCACGTCCACACTGCAAGCTTCTTCCGTATCAAC      520
421  S I K D I P I G I A R A V R T A V S G R P G G V Y V D L P A K L F
     AGCATCAAAGACATTCCAATCGGTATCGCTCGTGCAGTTCGCACCGCTGTATCCGGACGTCCAGGTGGTGTTTACGTTGACTTCCCAGCAAACTGTTCG  620
521  G Q T I S V E E A N K L L F K P I D P A P A Q I P A E D A I A R A A
     GTCAGACCATTTCTGTAGAAGAAGCTAACAAACTGCTCTTCAAACCAATCGATCCGGCACCAGCTCAGATCCCTGCTGAAGACGCTATCGCTCGCGCTGC  720
621  D L I K N A K R P V I M L G K G A A Y A Q C D D E I R A L V E E T
     TGACCTGATCAAGAACGCCAAACGTCCAGTTATCATGCTGGGTAAAGGCGCTGCATACGCACAATGCGACGACGAAATCCGGCACTGGTTGAAGAAACC  820
721  G I P F L P M G M A K G L L P D N H P Q S A A A T R A F A L A Q C
     GGCATCCCATTCCTGCCAATGGGTATGGCTAAAGGCCTAAAGGCCTGCTGCCTGACAACCATCCACAACCGTGCTTGCCACTGGCACAGTGTG          920
821  D V C V L I G A R L N W L M Q H G K T W G D E L K K Y V Q I D I
     ACGTTTGCGTACTGATCGGCGCTCGTCTGAACTGGCTGATGCAGCACGGTAAAGGCAAAACCTGGGGCGACGAACTGAAGAAATACGTTCAGATCGACAT
```

FIG. 3B

```
       Q  A  N  E  M  D  S  N  Q  P  I  A  A  P  V  V  G  D  I  K  S  A  V  S  L  L  R  K  A  L  K  G  A
 921 CCAGGCTAACGAAATGGACAGCAACCAGCCTATCGCTGCACCAGTTGTTGGTGACATCAAGTCCGCCGTTTCCCTGCTCCGCAAAGCACTGAAAGGCGCT 1020
       P  K  A  D  A  E  W  T  G  A  L  K  A  K  V  D  G  N  K  A  K  L  A  G  K  M  T  A  E  T  P  S  G
1021 CCAAAAGCTGACGCTGAATGGACCGGCGCTCTGAAAGCCAAAGTTGACGGCAACAAAGCCAAACTGGCTGGCAAGATGACTGCCGAAACCCCATCCGGAA 1120
       M  N  Y  S  N  S  L  G  V  V  R  D  F  M  L  A  N  P  D  I  S  L  V  N  E  G  A  N  A  L  D  N  T
1121 TGATGAACTACTACTCCAATTCCCTGGGCGTTGTTCGTGACTTCATGCTGGCAAATCCGGATATTTCCCTGGTTAACGAAGGCGCTAATGCACTCGACAACAC 1220
       R  M  I  V  D  M  L  K  P  R  K  R  L  D  S  G  T  W  G  V  M  G  I  G  M  G  Y  C  V  A  A  A
1221 TCGTATGATTGTTGACATGCTGAAACCGCGCAAACGTCTTGACTCCGGTACCTGGGGTGTGTTATGGGTATTGGTATGGGCTACTGCGTTGCTGCAGCTGCT 1320
                                                                    [----- TPP Binding Motif -----
       V  T  G  K  P  V  I  A  V  E  G  D  S  A  F  G  F  S  G  M  E  L  E  T  I  C  R  Y  N  L  P  V  T
1321 GTTACCGGCAAACCGGTTATCGCTGTTGAAGGCGATAGCGCATTCGGTTTCTCCGGTATGGAACTGGAAACCATCTGCCGTTACAACCTGCCAGTTACCG 1420
       V  I  I  M  N  G  G  I  Y  K  G  N  E  A  D  P  Q  P  G  V  I  S  C  T  R  L  T  R  G  R  Y  D  M
1421 GTTATCATCATGAACGGTGGTATCTATAAAGGTAACGAAGCAGATCCACAACCAGGCGTTATCTCCTGTACCCGTCTGACCCGTGGTCGTTACGACAT 1520
       M  E  A  F  G  G  K  G  Y  V  A  N  T  P  A  E  L  K  A  A  L  E  E  A  V  A  S  G  K  P  C  L
1521 GATGATGGAAGCATTTGGCGGTAAAGGTTATGTTGCCAATACTCCAGCAGAACTGAAAGCTGCTCTGGAAGAGCTGTTGCTTCCGGCAAACCATGCCTG 1620
       I  N  A  M  I  D  P  D  A  G  V  G  S  G  R  I  K  S  L  N  V  V  S  K  V  G  K  K
1621 ATCAACGCGATGATCGATCCAGACGCTGGTGTCGAATCTGGCCGTATCAAGAGCCTGAACGTTGTAAGTAAAGTTGGCAAGAAATAATTAGCCCAACTTT 1720
                                                                                          1705
1721 GATGACCGGTTACGACCGGTCACATAAAGTGTTCGAATGCCCTTCAAGTTACTTGAAGGCATTTTTTTACCTTGCAGTTTATAAACAGGAAAAATTGT 1820
                            1758
1821 ATTCAGAGCGGGAAAAGCAGATTTAAGCCACGAGAAACATTCTTTTTATTGAAAATTGCCATAAACACATTTTAAAGCTGGCTTTT 1908
```

METHOD AND KIT FOR DETECTION OF OXALATE

BACKGROUND OF THE INVENTION

The present invention relates to novel assay methods for determining the presence or concentration of oxalate in a sample. The present invention further relates to the cloning, sequencing and expression of formyl-CoA transferase, an enzyme used in the novel assay for the detection of oxalate.

Oxalic acid (Oxalate) is a highly toxic natural by-product of catabolism in vertebrate animals and many consumable plants. Unfortunately, a significant portion of humans are unable to properly metabolizing oxalate, a condition which may result in the formation of kidney stones in those persons. It is estimated that 70% of all kidney stones are composed of some amount of oxalate. Approximately 12 percent of the U.S. population will suffer from a kidney stone at some time in their lives, and the incidence is rising not only in the United States, but also in Sweden and Japan (Curhan, 1993). Moreover, although a healthy person breaks down or excretes sufficient quantities of oxalate to avoid excessive accumulation of oxalate in the tissues, a number of disease states are known to be associated with malfunctions of oxalate metabolism, including pyridoxine deficiency, renal failure and primary hyperoxaluria, a metabolic genetic disorder that results in the excessive deposition of oxalate in the kidneys.

Persons suffering from and at risk for developing kidney stones, as well as patients with lipid malabsorption problems (e.g., sprue, pancreatic insufficiency, inflammatory intestinal disease, bowel resection, etc.), tend to have elevated levels of urinary oxalate, a fact that has been exploited as a means for identifying individuals at risk. While elevated levels of oxalate may be present in urine, detecting elevated levels of oxalate in serum has not been routine due to the difficulty in detecting the low levels of oxalate present in serum.

Most previous methods for measuring oxalate in a biological sample first require the isolation of the oxalate by precipitation, solvent extraction, or an ion-exchange absorption (Hodgkinson, 1970). Quantitation of the isolated oxalate may be determined by any one of several methods including colorimetry, fluorometry, gas-liquid chromatography or isotope dilution techniques. Because many of the oxalate isolation techniques used in these analytical methods are not quantitative, it is normally necessary to correct for the low recovery of oxalate by adding a $^{14}C$-labeled oxalic acid internal standard, which further complicates the analytical method. All these methods are laborious, and consequently expensive because of the amount of skilled laboratory technician time which must be employed. In addition, isolation of the oxalate may require relatively large sample volumes for starting material.

Recently, several advances in the detection and quantitation of oxalate have been made through the use of (a) oxalate degrading enzymes and (b) high performance liquid chromatography. One commercially-available enzymatic test (Sigma Chemical Company, St. Louis, Mo.) employs oxalate oxidase to oxidize oxalate to carbon dioxide and hydrogen peroxide. The hydrogen peroxide produced can then be measured colorimetrically in a second enzymatic reaction in the presence of peroxidase.

In another enzymatic method for measuring oxalate, oxalate decarboxylase is used to convert oxalate to carbon dioxide and formate. The resultant carbon dioxide can be measured manometrically, by the pH change in a carbon dioxide trapping buffer or by the color change in a pH indicator buffer. Whatever method of carbon dioxide assay is adopted, the time required for diffusion and equilibration of carbon dioxide is much longer than is desirable for a rapid analytical method.

Alternatively, the formate produced by the action of oxalate decarboxylase can be assayed with formate dehydrogenase in an NAD/NADH coupled reaction, as described in Costello, 1976 and Yriberri, 1980. This method is both cumbersome and time-consuming because oxalate decarboxylase and formate dehydrogenase differ in their optimum pH requirements, thus necessitating a pH adjustment during the analysis.

Another commercially available enzymatic test (Boehringer Mannheim) cleaves oxalate to formate and carbon dioxide, then oxidizes the formate to bicarbonate by NAD in the presence of the enzyme formate dehydrogenase. The amount of NADH is determined by means of its absorbance at 334, 340, or 365 nm. Another test ("STONE RISK" by Mission Pharmacal) measures oxalate as a part of a battery of tests for kidney stones.

As illustrated above, the currently existing assays for oxalate suffer from numerous problems, including cost, inaccuracy, reliability, complexity, and lack of sensitivity. Accordingly, it is an object of the subject invention to provide a simple, accurate, and sensitive assay for the detection of low levels of oxalate in a biological sample.

BRIEF SUMMARY OF THE INVENTION

The subject invention concerns the cloning, sequencing, and expression of the formyl-CoA transferase and the oxalyl-CoA decarboxylase genes of *Oxalobacter formigenes,* and the use of the enzymes to detect the presence of oxalate in a sample. The assay of the subject invention provides, for the first time, a rapid, sensitive method to detect even very low concentrations of oxalate in biological samples. Advantageously, the biological samples in which oxalate can be detected include both urine and serum samples. The enzyme system used according to the subject invention converts oxalate to carbon dioxide and formate. In a preferred embodiment of the subject invention, the production of formate is then measured colorimetrically. This assay provides a sensitive, accurate and convenient means for detecting oxalate.

A further aspect of the subject invention is the discovery of the *O. formigenes* genes which encode the formyl-CoA transferase and the oxalyl-CoA decarboxylase enzymes. The discovery of these genes makes it possible to efficiently produce large quantities of pure formyl-CoA transferase and oxalyl-CoA decarboxylase for use in the assay of the subject invention or other appropriate application.

BRIEF SUMMARY OF THE FIGURES

FIG. 2 shows a partial nucleotide sequence of the formyl-CoA transferase gene.

FIGS. 3A and 3B show the nucleotide sequence of the oxalyl-CoA decarboxylase gene and flanking regions. The consensus ribosome-binding site lies approximately 10 bases upstream (double-underlined letters) from the putative translation initiation codon (positions 1 to 3). A rho-independent termination sequence lies at positions 1758 to 1790 (double-underlined letters). A putative TPP-binding site appears between positions 1351 and 1437.

BRIEF DESCRIPTION OF THE SEQUENCES

Figure 1A:
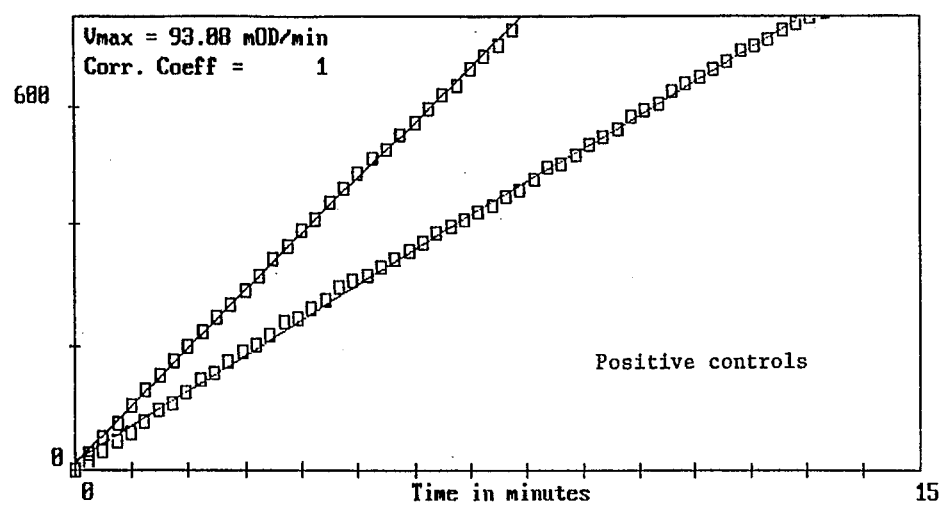
FIGS. 1A–1E shows the detection of varying concentrations of oxalate in a sample. Colorimetric absorbance for each sample was plotted over time (minutes). Positive and negative control panels are also shown.
Figure 1B:
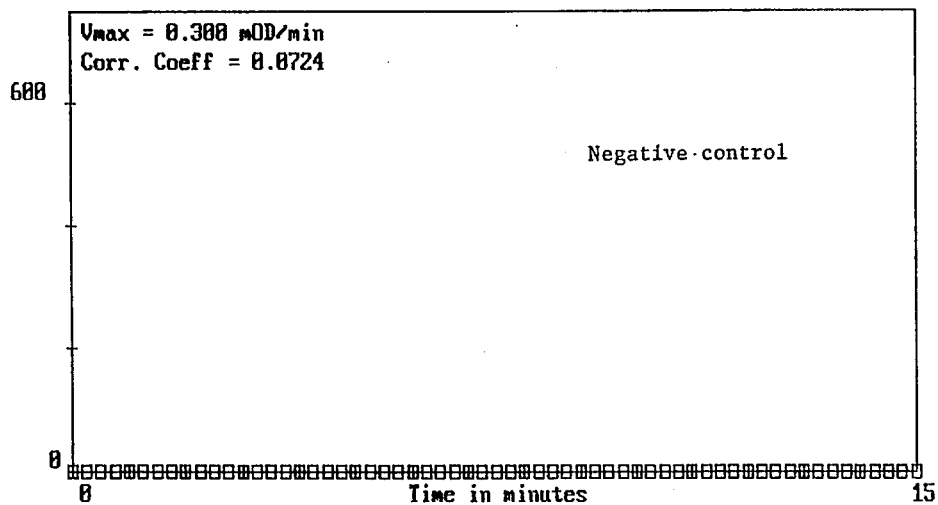
Figure 1C:
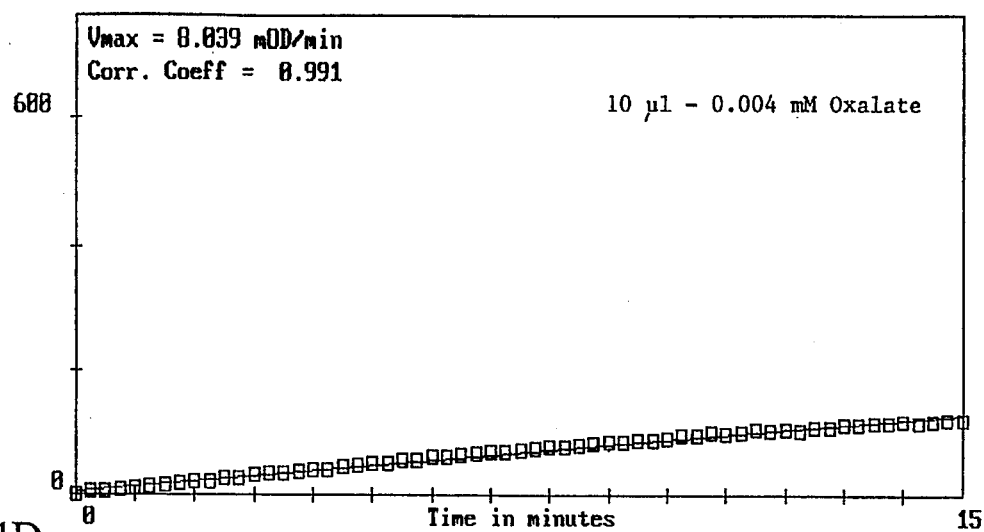
Figure 1D:
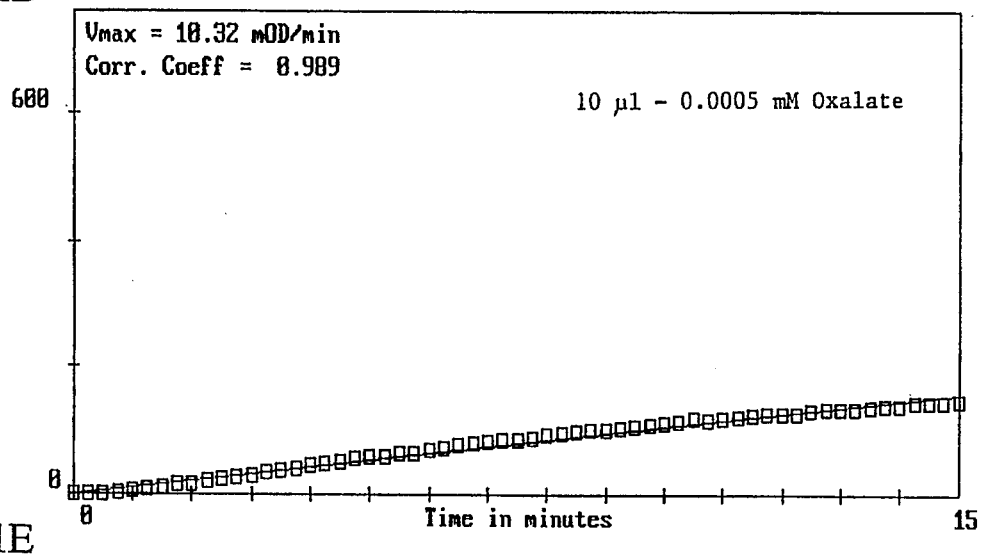

SEQ ID NOS. 1–3 are the known parts of the nucleotide sequence for the formyl-CoA transferase gene (also shown in FIG. 2).

SEQ ID NO. 4 is a polypeptide encoded by SEQ ID NO. 1, which can be used according to the subject invention.

SEQ ID NO. 5 is a polypeptide encoded by SEQ ID NO. 2, which can be used according to the subject invention.

SEQ ID NO. 6 is the nucleotide sequence for the oxalyl-CoA decarboxylase gene (also shown in FIG. 3).

SEQ ID NO. 7 is a polypeptide encoded by SEQ ID NO. 6, which can be used according to the subject invention.

DETAILED DESCRIPTION OF THE INVENTION

The subject invention provides an accurate, sensitive assay for oxalate in biological samples such as urine and serum. Elevated levels of oxalate are correlated with urinary tract stone formation, as well as other health problems. Early detection of high levels of oxalate makes it possible to prevent, delay or reduce adverse health consequences through appropriate medication and through modulation of diet.

In the presently described diagnostic system, two enzymes are used to catabolize oxalate to carbon dioxide and formate. Specifically, any oxalate that may be present in a sample being assayed is converted into formate and carbon dioxide ($CO_2$) through the combined action of the enzymes oxalyl-CoA decarboxylase and formyl-CoA transferase. The formate can then be detected using a variety of techniques known in the art. In a preferred embodiment, the production of formate is measured colorimetrically by linking the catabolism of formate with the production of a detectable color change (for example, the formation of a compound that absorbs a particular wavelength of light). The production of formate is directly correlated with the amount of oxalate present in the sample. Therefore, if a known amount of formate is produced using the subject enzyme system, then the amount of oxalate present in the sample can be easily quantitated.

In a preferred embodiment, the enzymes used in the subject invention are expressed by genes from the bacterium *Oxalobacter formigenes*. The genes encoding both oxalyl-CoA decarboxylase (Lung, 1994) and formyl-CoA transferase enzymes have been cloned and expressed, thus providing a readily-available source of reagent material. The subject assay is capable of detecting oxalate levels in a range as low as 0.00025–0.0005 mM (FIG. 1A–1E). This level of sensitivity makes the subject assay capable of direct detection of oxalate in serum samples consisting of little as 10 μl volume. The described system can be easily automated with standard systems known in the art.

In a preferred embodiment of the subject assay, the enzymatic reaction can be carried out in the wells of flat-bottomed 96-well microtiter plates and read in an automated plate reader. Suitable concentrations of the assay reagents oxalyl-CoA decarboxylase, oxalyl-CoA, β-NAD, formate dehydrogenase, and the sample to be assayed are added to the microtiter wells. The reaction is then brought to equilibrium (two minute incubation at 37° centigrade in the plate reader) to permit degradation of any residual formate that may be present in the sample. The formyl-CoA transferase enzyme is then added to the mixture to start the reaction, and the plate is read at 15 second intervals. Formate production is determined by measuring the reduction in NAD in the presence of formate dehydrogenase by detecting changes in absorbance of the sample at 340 nm (Baetz and Allison, 1989). The quantity of oxalate is determined by comparison of the unknown samples with standards having a known amount of oxalate.

Further, the enzymatic reaction of the subject assay will not be initiated until the formyl-CoA transferase, oxalyl-CoA decarboxylase, and oxalyl-CoA are all present within the reaction mixture. Therefore, initiation of the enzymatic reaction can be prevented by withholding one of the above reagents from the reaction mix. Preferably, oxalyl-CoA decarboxylase and oxalyl-CoA are added first, and the reaction is initiated by the addition of formyl-CoA transferase to the mix. However, the order of addition of the three reagents is not material to the function of the assay, so long as one of the reagents is withheld until just prior to the desired initiation point of the assay.

The formyl-CoA transferase and oxalyl-CoA decarboxylase enzyme used in the subject invention can be obtained and purified as a natural product of *Oxalobacter formigenes* (Baetz and Allison, 1989 and 1990). Alternatively, the enzymes can be obtained from host cells expressing the recombinant polynucleotide molecules of the subject invention that encode the enzymes. Other reagents used in the subject assay can be obtained from conventional sources, such as Sigma Chemical Company, St. Louis, Mo. Further, a person of ordinary skill in the art can readily determine the optimal concentrations of the reagents to use in the assay described herein.

A further aspect of the subject invention concerns the cloning, sequencing and expression of the *Oxalobacter formigenes* gene which encodes the formyl-CoA transferase used in the assay that is a subject of the invention. The gene was cloned using degenerate oligonucleotide probes (based on partial amino acid sequencing of tryptic peptides) to screen an Oxalobacter genomic DNA library. The gene encodes a polypeptide having a molecular weight of approximately 40 kD. The subject invention further concerns the cloning, sequencing, and expression of the gene which encodes oxalyl-CoA decarboxylase from *Oxalobacter formigenes*. The nucleotide sequence of the cDNA of formyl-CoA transferase and oxalyl-CoA decarboxylase are shown in FIGS. 2, 3A and 3B, respectively (SEQ ID NOS. 1–3 and 6)

Because of the redundancy of the genetic code, a variety of different polynucleotide sequences can encode the formyl-CoA transferase polypeptide disclosed herein. It is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional enzymatic activity of the encoded polypeptide. Further, the subject invention contemplates those polynucleotide molecules having sequences which are sufficiently homologous with the DNA sequences shown in FIGS. 2, 3A and 3B (SEQ ID NOS. 1–3 and 6) so as to permit hybridization with those sequences under standard high-stringency conditions. Such hybridization conditions are conventional in the art (see, e.g., Maniatis et al., 1989).

As a person skilled in the art would appreciate, certain amino acid substitutions within the amino acid sequence of the polypeptide can be made without altering the functional activity of the enzyme. For example, amino acids may be placed in the following classes: non-polar, uncharged polar, basic, and acidic. Conservative substitutions, whereby an amino acid of one class is replaced with another amino acid of the same class, fall within the scope of the subject invention so long as the substitution does not materially alter the enzymatic reactivity of the polypeptide. Non-conservative substitutions are also contemplated as long as the substitution does not significantly alter the functional activity of the encoded polypeptide.

The polynucleotides of the subject invention can be used to express the recombinant formyl-CoA transferase enzyme. They can also be used as a probe to detect related enzymes. The polynucleotides can also be used as DNA sizing standards.

The polypeptides encoded by the polynucleotides can be used to raise an immunogenic response to the formyl-CoA transferase enzyme. They can also be used as molecular weight standards, or as inert protein in an assay. The polypeptides can also be used to detect the presence of antibodies immunoreactive with the enzyme.

The polynucleotide sequences of the subject invention may be composed of either RNA or DNA. More preferably, the polynucleotide sequences are composed of DNA.

Another aspect of the subject invention pertains to kits for carrying out the enzyme assay for oxalate. In one embodiment, the kit comprises, in packaged combination and in relative quantities to optimize the sensitivity of the described assay method, (a) the oxalyl-CoA decarboxylase, oxalyl-CoA, β-NAD, and formate dehydrogenase; and (b) formyl-CoA transferase. The kit may optionally include other reagents or solutions, such as buffering and stabilization agents, along with any other reagents that may be required for a particular signal generation system. Other reagents such as positive and negative controls can be included in the kit to provide for convenience and standardization of the assay method.

Following are examples which illustrate procedures, including the best mode, for practicing the invention. These examples should not be construed as limiting. All percentages are by weight and all solvent mixture proportions are by volume unless otherwise noted.

EXAMPLE 1

Determination of Level of Sensitivity of Enzyme Assay System

Figure 1E:
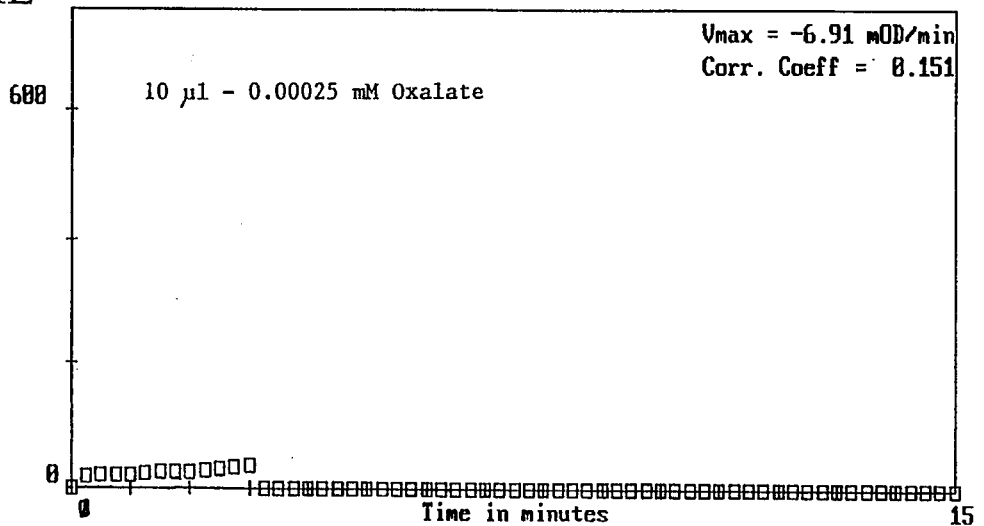

Samples containing oxalate at concentrations ranging from 0.004 mM to 0.00025 mM were prepared in 10 μl volumes. The samples were then assayed using the enzyme system of the subject invention in 96-well microtiter plates. Reagents were then added at the following concentrations: $KH_2PO_4$ (pH 6.7), 50 mM; $MgCl_2$, 5 mM; thiamine PPi (TPP), 2 mM; oxalyl-CoA, 0.375 mM; β-NAD, 1.0 mM; formate dehydrogenase, 0.25 IU; and oxalyl-CoA decarboxylase, 0.03 U. The reaction mixture was then incubated at 37° C. for 2 minutes in order to permit the degradation of any residual formate that may be present in the sample mixture. The reaction was then initiated by the addition of formyl-CoA transferase to the, sample mixture. Changes in $A_{340}$ were measured every 15 seconds at 37° C. (FIG. 1A and 1E). Appropriate positive and negative controls were run simultaneously with the assay.

It should be understood that the examples and embodiments described herein are for illustrative purposes only and that various modifications or changes in light thereof will be suggested to persons skilled in the art and are to be included within the spirit and purview of this application and the scope of the appended claims.

References

Baetz, A. L., M. J. Allison (1989) "Purification and Characterization of Oxalyl-Coenzyme A Decarboxylase from *Oxalobacter formigenes*," *J. Bacteriol.* 171:2605–2608.

Baetz, A. L., M. J. Allison (1990) "Purification and Characterization of Formyl-Coenzyme A Transferase from *Oxalobacter formigenes*," *J. Bacteriol.* 172:3537–3540.

Curhan, et al. (1993) "A Prospective study of dietary calcium and other nutrients and the risk of symptomatic kidney stones," *N. E. J. Med.* 328:833–838.

Costello, J., M. Hatch, E. Bourke (1976) "An enzymic method for the spectrophotometric determination of oxalic acid," *J. Lab. Clin. Med.* 87(5):903–908.

Hodgkinson, A. (1970) "Determination of Oxalic acid in Biological Material," *Clin. Chem.* 16(7):547–557.

Lung, H., A. L. Baetz, A. B. Peck (1994) "Molecular Cloning, DNA Sequence and Gene Expression of the Oxalyl-CoA Decarboxylase Gene, oxc, from the Bacterium *Oxalobacter formigenes*," *J. Bacteriol.* 176(8):2468–2472.

Maniatis, T., E. F. Fritsch, J. Sambrook (1989) *Molecular Cloning: A Laboratory Manual*, 2d Edition, Cold Spring Harbor Laboratory, Cold Spring Harbor, N.Y.

Yriberri, J., L. S. Posten (1980) "A semi-automatic enzymic method for estimating urinary oxalate," *Clin. Chem.* 26(7):881–884.

---

I claim:

1. A method for detecting a presence of oxalate in a fluid sample, comprising the steps of:
   (a) contacting said fluid sample with oxalyl-CoA decarboxylase formyl-CoA transferase to form an admixture, wherein any oxalate present in said admixture is converted into carbon dioxide and formate; and
   (b) detecting any said formate produced in said admixture
   (c) correlating detecting any said formate with the presence of oxalate in the fluid sample.

2. The method, according to claim 1, wherein step (a) further comprises contacting said fluid sample with oxalyl-CoA.

3. The method, according to claim 2, wherein step (a) further comprises contacting said sample with NAD and formate dehydrogenase.

4. A method for detecting a presence of oxalate in a fluid sample, comprising the steps of:
   (a) contacting said sample with oxalyl-CoA decarboxylase, oxalyl-CoA, β-NAD, and formate dehydrogenase to form a first admixture;
   (b) contacting said first admixture with formyl-CoA transferase to form a second admixture, wherein any oxalate present in said second admixture is converted into carbon dioxide and formate, and said formate reduces said NAD to NADH;
   (c) detecting any said NADH produced in said second admixture,
   (d) correlating detecting any said NADH with the presence of oxalate in the fluid sample.

5. The method, according to claim 4, wherein said NADH is detected colorimetrically by measuring absorbance of said second admixture at about 334, 340, or 365 nm.

6. A kit for detecting the presence or concentration of oxalate in a fluid sample, comprising in one or more containers:

(a) oxalyl-CoA decarboxylase, oxalyl-CoA, β-NAD, and formate dehydrogenase; and (b) formyl-CoA transferase.

* * * * *

UNITED STATES PATENT AND TRADEMARK OFFICE
CERTIFICATE OF CORRECTION

PATENT NO. : 5,604,111

DATED : February 18, 1997

INVENTOR(S) : Ammon B. Peck

It is certified that error appears in the above-indentified patent and that said Letters Patent is hereby corrected as shown below:

Column 4: Line 40: "1-3 and 6)" should read --1-3 and 6).--
Column 6: Line 9: "the, sample" should read --the sample--.

Signed and Sealed this

Fifteenth Day of July, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,604,111
DATED         : February 18, 1997
INVENTOR(S)   : Ammon B. Peck It is certified that error appears in the above-identified patent and that said Letters Patent is hereby corrected as shown below:

Column 1,
Lines 1-5,
"METHOD AND KIT FOR DETECTION OF OXALATE

BACKGROUND OF THE INVENTION"
should read
-- METHOD AND KIT FOR DETECTION OF OXALATE This invention was made with government support under National Institutes of Health Grant No. DK 20586. The government has certain rights in this invention.

BACKGROUND OF THE INVENTION --.

Signed and Sealed this

Twenty-eighth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,604,111  Page 1 of 1
DATED : February 18, 1997
INVENTOR(S) : Ammon B. Peck It is certified that error appears in the above-identified patent and that said Letters Patent is hereby corrected as shown below:

Column 13,
Lines 56 and 57, "decarboxylase formyl-CoA transferase" should read -- decarboxylase and formyl-CoA transferase --.
Line 59, "in said admixture" should read -- in said admixture; and --.

Column 14,
Lines 64 and 65, "said second admixture," should read -- said second admixture; and --.

Signed and Sealed this

Fourteenth Day of October, 2003

JAMES E. ROGAN
*Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATGACNAARC  CNYTNGAYGG  NATHAAYGTN  YTNGAYTTYA  CNCAYGTNCA  RGCNGGNCCN      60
GCN                                                                         63
```

( 2 ) INFORMATION FOR SEQ ID NO:2:

( i ) SEQUENCE CHARACTERISTICS:
            ( A ) LENGTH: 567 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| CGACTGTGAT | ATATGCGAAC | TGCAGTGGTC | TGATATCTGA | GATGGATATC | TTTATGTCGA | 60 |
| GCAAAGCCCC | ACAGGCGTAA | AAATTGCCAT | CCCAACAGCA | TTGCATATTG | ATGCTCTCGG | 120 |
| AATAACAATG | AAGGAAACAC | TTGATAAATG | CAAAGAGATT | CTTGGCGGAG | AAACCATAAT | 180 |
| TGCATCTACT | CGTCGCGAAC | CGCTTTCATC | CGGCACAGTA | TCAAGGTATT | TTATGCGCGC | 240 |
| ACGAAAAGCA | TCAGGTCTTT | CCTTCGAAGG | GGATACTCTA | GAACCTTGTC | GACGTCCTGC | 300 |
| CTGTACACAG | ATGATGGGTT | TCTTGGGCGC | AAACGTCATC | AAGATTGAAA | GACGTGGTTC | 360 |
| CGGAGATATG | ACTCGTGGAT | GCTGCAGGAC | AAACCAAATG | TTGATTCCCT | GTATTTCACG | 420 |
| ATGTTCAACT | GTAACAAACG | TTCGATTGAA | CTGGACATGA | AACCCCGGA | AGGCAAAGAG | 480 |
| CTTCTGGAAC | AGATGATCAA | GAAAGCCGAC | GTCATGGTCG | AAAACTTCGG | ACCAGGCGCA | 540 |
| CTGGACCGTA | TGGGCTTTAC | CTGGGCC | | | | 567 |

( 2 ) INFORMATION FOR SEQ ID NO:3:

( i ) SEQUENCE CHARACTERISTICS:
            ( A ) LENGTH: 281 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| CTTAACCGAA | CCAGCGTCGA | AGATGGTATT | TCAATGAAAA | CAACAACCCC | GTCATTATCC | 60 |
| GGACTGCCGG | AAATCTCGAT | TGTAACGACG | GAGAACTCCT | GCACCGTTGG | TGTCTGGAAG | 120 |
| GATATGGGCT | GGCCTGGCTG | TCGACATGGG | AAATACAATC | CGAACTCGCC | CGGTAAACTG | 180 |
| GTCACCGTAC | TGGACGATTA | CGCCCTTCCC | AACTACGACA | TCATGGGAGT | TTACCCCCAC | 240 |
| GAAAGATCCC | TCCCCTTGAA | AACCCGTCTG | TCCATGTCCG | G | | 281 |

( 2 ) INFORMATION FOR SEQ ID NO:4:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:4:

Met Thr Lys Pro Leu Asp Gly Ile Asn Val Leu Asp Phe Thr His Val
      1               5                     10                   15

Gln Ala Gly Pro Ala
                  20

( 2 ) INFORMATION FOR SEQ ID NO:5:

( i ) SEQUENCE CHARACTERISTICS:
            ( A ) LENGTH: 43 amino acids (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:5:

Arg Ser Ile Glu Leu Asp Met Lys Thr Pro Glu Gly Lys Glu Leu Leu
1               5                   10                  15

Glu Gln Met Ile Lys Lys Ala Asp Val Met Val Glu Asn Phe Gly Pro
            20                  25                  30

Gly Ala Leu Asp Arg Met Gly Phe Thr Trp Ala
            35                  40

(2) INFORMATION FOR SEQ ID NO:6:

(i) SEQUENCE CHARACTERISTICS:
      (A) LENGTH: 2088 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:6:

| | | | | | | |
|---|---|---|---|---|---|---|
| ATTTGTTTAA | ATTGACCTGA | ATCAATATTG | CCGGATTGAT | CTAGGTCAAT | GAATGCAAAT | 60 |
| TGACTTATGT | CAATGGTGCC | AAATTGACCT | AGGTCAACGG | GATTTTAAA | GGGTATGCGG | 120 |
| CATACTCGGA | ATTGACGTTA | AACAACGTTT | ATCAAAACCA | ACCAAGAAA | GGTATTACTC | 180 |
| ATGAGTAACG | ACGACAATGT | AGAGTTGACT | GATGGCTTTC | ATGTTTTGAT | CGATGCCCTG | 240 |
| AAAATGAATG | ACATCGATAC | CATGTATGGT | GTTGTCGGCA | TTCCTATCAC | GAACCTGGCT | 300 |
| CGTATGTGGC | AAGATGACGG | TCAGCGTTTT | TACAGCTTCC | GTCACGAACA | ACACGCAGGT | 360 |
| TATGCAGCTT | CTATCGCCGG | TTACATCGAA | GGAAAACCTG | GCGTTTGCTT | GACCGTTTCC | 420 |
| GCCCCTGGCT | TCCTGAACGG | CGTGACTTCC | CTGGCTCATG | CAACCACCAA | CTGCTTCCCA | 480 |
| ATGATCCTGT | TGAGCGGTTC | CAGTGAACGT | GAAATCGTCG | ATTTCCAAGA | CGGCGATTAC | 540 |
| GAAGAAATGG | ATCAGATGAA | TGTTGCACGT | CCACACTGCA | AGCTTCTTT | CCGTATCAAC | 600 |
| AGCATCAAAG | ACATTCCAAT | CGGTATCGCT | CGTGCAGTTC | GCACCGCTGT | ATCCGGACGT | 660 |
| CCAGGTGGTG | TTTACGTTGA | CTTCCCAGCA | AAACTGTTCG | GTCAGACCAT | TTCTGTAGAA | 720 |
| GAAGCTAACA | AACTGCTCTT | CAAACCAATC | GATCCAGCTC | CGGCACAGAT | TCTTGCTGAA | 780 |
| GACGCTATCG | CTCGCGCTGC | TGACCTGATC | AAGAACGCCA | AACGTCCAGT | TATCATGCTG | 840 |
| GGTAAAGGCG | CTGCATACGC | ACAATGCGAC | GACGAAATCC | GCGCACTGGT | TGAAGAAACC | 900 |
| GGCATCCCAT | TCCTGCCAAT | GGGTATGGCT | AAAGGCCTGC | TGCCTGACAA | CCATCCACAA | 960 |
| TCCGCTGCTG | CAACCCGTGC | TTTCGCACTG | GCACAGTGTG | ACGTTTGCGT | ACTGATCGGC | 1020 |
| GCTCGTCTGA | ACTGGCTGAT | GCAGCACGGT | AAAGGCAAAA | CCTGGGGCGA | CGAACTGAAG | 1080 |
| AAATACGTTC | AGATCGACAT | CCAGGCTAAC | GAAATGGACA | GCAACCAGCC | TATCGCTGCA | 1140 |
| CCAGTTGTTG | GTGACATCAA | GTCCGCCGTT | TCCCTGCTCC | GCAAAGCACT | GAAGGCGCT | 1200 |
| CCAAAAGCTG | ACGCTGAATG | GACCGGCGCT | CTGAAGCCA | AAGTTGACGG | CAACAAAGCC | 1260 |
| AAACTGGCTG | GCAAGATGAC | TGCCGAAACC | CCATCCGGAA | TGATGAACTA | CTCCAATTCC | 1320 |
| CTGGGCGTTG | TTCGTGACTT | CATGCTGGCA | AATCCGGATA | TTTCCCTGGT | TAACGAAGGC | 1380 |
| GCTAATGCAC | TCGACAACAC | TCGTATGATT | GTTGACATGC | TGAAACCACG | CAAACGTCTT | 1440 |
| GACTCCGGTA | CCTGGGGTGT | TATGGGTATT | GGTATGGGCT | ACTGCGTTGC | TGCAGCTGCT | 1500 |

```
GTTACCGGCA AACCGGTTAT CGCTGTTGAA GGCGATAGCG CATTCGGTTT CTCCGGTATG    1560

GAACTGGAAA CCATCTGCCG TTACAACCTG CCAGTTACCG TTATCATCAT GAACAATGGT    1620

GGTATCTATA AAGGTAACGA AGCAGATCCA CAACCAGGCG TTATCTCCTG TACCCGTCTG    1680

ACCCGTGGTC GTTACGACAT GATGATGGAA GCATTTGGCG GTAAAGGTTA TGTTGCCAAT    1740

ACTCCAGCAG AACTGAAAGC TGCTCTGGAA GAAGCTGTTG CTTCCGGCAA ACCATGCCTG    1800

ATCAACGCGA TGATCGATCC AGACGCTGGT GTCGAATCTG GCCGTATCAA GAGCCTGAAC    1860

GTTGTAAGTA AAGTTGGCAA GAAATAATTA GCCCAACTTT GATGACCGGT TACGACCGGT    1920

CACATAAAGT GTTCGAATGC CCTTCAAGTT TACTTGAAGG GCATTTTTTT ACCTTGCAGT    1980

TTATAAACAG GAAAAATTGT ATTCAGAGCG GAAAGCAGA TTTAAGCCAC GAGAAACATT     2040

CTTTTTTATT GAAAATTGCC ATAAACACAT TTTTAAAGCT GGCTTTTT               2088
```

( 2 ) INFORMATION FOR SEQ ID NO:7:

( i ) SEQUENCE CHARACTERISTICS:
    ( A ) LENGTH: 568 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Met Ser Asn Asp Asp Asn Val Glu Leu Thr Asp Gly Phe His Val Leu
 1               5                  10                   15

Ile Asp Ala Leu Lys Met Asn Asp Ile Asp Thr Met Tyr Gly Val Val
             20                  25                  30

Gly Ile Pro Ile Thr Asn Leu Ala Arg Met Trp Gln Asp Asp Gly Gln
             35                  40                  45

Arg Phe Tyr Ser Phe Arg His Glu Gln His Ala Gly Tyr Ala Ala Ser
         50                  55                  60

Ile Ala Gly Tyr Ile Glu Gly Lys Pro Gly Val Cys Leu Thr Val Ser
 65                  70                  75                  80

Ala Pro Gly Phe Leu Asn Gly Val Thr Ser Leu Ala His Ala Thr Thr
                 85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
            115                 120                 125

Ala Arg Pro His Cys Lys Ala Ser Phe Arg Ile Asn Ser Ile Lys Asp
        130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
            195                 200                 205

Leu Ile Lys Asn Ala Lys Arg Pro Val Ile Met Leu Gly Lys Gly Ala
        210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255
```

```
Asn His Pro Gln Ser Ala Ala Ala Thr Arg Ala Phe Ala Leu Ala Gln
            260                 265             270
Cys Asp Val Cys Val Leu Ile Gly Ala Arg Leu Asn Trp Leu Met Gln
        275             280                 285
His Gly Lys Gly Lys Thr Trp Gly Asp Glu Leu Lys Lys Tyr Val Gln
    290             295             300
Ile Asp Ile Gln Ala Asn Glu Met Asp Ser Asn Gln Pro Ile Ala Ala
305             310             315                         320
Pro Val Val Gly Asp Ile Lys Ser Ala Val Ser Leu Leu Arg Lys Ala
            325             330                         335
Leu Lys Gly Ala Pro Lys Ala Asp Ala Glu Trp Thr Gly Ala Leu Lys
        340             345             350
Ala Lys Val Asp Gly Asn Lys Ala Lys Leu Ala Gly Lys Met Thr Ala
        355             360             365
Glu Thr Pro Ser Gly Met Met Asn Tyr Ser Asn Ser Leu Gly Val Val
    370             375             380
Arg Asp Phe Met Leu Ala Asn Pro Asp Ile Ser Leu Val Asn Glu Gly
385             390             395                         400
Ala Asn Ala Leu Asp Asn Thr Arg Met Ile Val Asp Met Leu Lys Pro
            405             410                     415
Arg Lys Arg Leu Asp Ser Gly Thr Trp Gly Val Met Gly Ile Gly Met
        420             425                 430
Gly Tyr Cys Val Ala Ala Ala Val Thr Gly Lys Pro Val Ile Ala
        435             440             445
Val Glu Gly Asp Ser Ala Phe Gly Phe Ser Gly Met Glu Leu Glu Thr
    450             455             460
Ile Cys Arg Tyr Asn Leu Pro Val Thr Val Ile Ile Met Asn Asn Gly
465             470             475             480
Gly Ile Tyr Lys Gly Asn Glu Ala Asp Pro Gln Pro Gly Val Ile Ser
            485             490             495
Cys Thr Arg Leu Thr Arg Gly Arg Tyr Asp Met Met Met Glu Ala Phe
        500             505             510
Gly Gly Lys Gly Tyr Val Ala Asn Thr Pro Ala Glu Leu Lys Ala Ala
        515             520             525
Leu Glu Glu Ala Val Ala Ser Gly Lys Pro Cys Leu Ile Asn Ala Met
    530             535             540
Ile Asp Pro Asp Ala Gly Val Gly Ser Gly Arg Ile Lys Ser Leu Asn
545             550             555             560
Val Val Ser Lys Val Gly Lys Lys
                565
```